US008233684B2

(12) United States Patent
Licato et al.

(10) Patent No.: US 8,233,684 B2
(45) Date of Patent: Jul. 31, 2012

(54) SYSTEMS AND METHODS FOR AUTOMATED DIAGNOSIS

(75) Inventors: Paul Licato, Wauwatosa, WI (US); Laurent Launay, St. Remy Chevreuse (FR); Saad Sirohey, Pewaukee, WI (US); Olga Imas, Milwaukee, WI (US)

(73) Assignee: General Electric Company, Schenectady, NY (US)

( * ) Notice: Subject to any disclaimer, the term of this patent is extended or adjusted under 35 U.S.C. 154(b) by 866 days.

(21) Appl. No.: 12/324,106

(22) Filed: Nov. 26, 2008

(65) Prior Publication Data

US 2010/0128942 A1 May 27, 2010

(51) Int. Cl.
*G06K 9/00* (2006.01)
(52) U.S. Cl. ........................................................ 382/128
(58) Field of Classification Search .................. None
See application file for complete search history.

(56) References Cited

U.S. PATENT DOCUMENTS

| 7,027,630 | B2 | 4/2006 | Bruijns |
| 7,123,760 | B2 | 10/2006 | Mullick et al. |
| 7,606,345 | B2 * | 10/2009 | Nishide et al. ............ 378/4 |
| 8,098,914 | B2 * | 1/2012 | Liao et al. ............ 382/128 |
| 2005/0147297 | A1 | 7/2005 | McLaughlin et al. |
| 2005/0259854 | A1 | 11/2005 | Arimura et al. |
| 2006/0079743 | A1 | 4/2006 | Ferrant et al. |
| 2007/0129627 | A1 | 6/2007 | Profio et al. |
| 2008/0118127 | A1 * | 5/2008 | Sirohey et al. ............ 382/130 |

OTHER PUBLICATIONS

Hirai, Toshinori, et al., Intracranial Aneurysms at MR Angiography: Effect of Computer-aided Diagnosis on Radiologists' Detection Performance. Radiology 2005; 237:605-610. Http://radiology.rsnajnls.org/cgi/content/abstract/237/2/605.
Doi, K., Current Status and Future Potential of Computer-aided Diagnosis in Medical Imaging. The British Journal of Radiology, 78 (2005), S3-S19. Http://bjr.birjournals.org/cgi/content/abstract/78/suppl_1/S3.
Hisanori, Hayashi, et al., Development of Cerebral Aneurysm Computer-Aided Detection Systems with 3D MRA Data. Yokogawa Technical Report English Edition, No. 39 (2005). Http://www.yokogawa.com/rd/pdf/TR/rd-tr-r00039-008.pdf.
Kobashi, Syoji, et al. "Computer-Aided Diagnosis of Intracranial Aneurysms in MRA Images with Case-Based Reasoning." IEICE Transactions on Information and Systems, Jul. 6, 2005. Abstract, http://ietisy.oxfordjournals.org/cgi/content/abstract/E89-D/1/340.
Uchiyama, Y. et al., "Computer-Aided Diagnosis Scheme for Detection of Unruptured Intracranial Aneurysms in MR Angiography." Engineering in Medicine and Biology Society, 2005. Abstract, http://ieeexplore.ieee.org/xpl/freeabs_all.jsp?arnumber=1617113.
Maintz, J.B. Antoine, et al., An Overview of Medical Image Registration Methods. No date given. Http://people.cs.uu.nl/twan/personal/brussel_bvz.pdf.
Meijering, Erik H.W., et al., Image Registration for Digital Subtraction Angiography. International Journal of Computer Vision, vol. 31, No. 2/3, Apr. 1999, pp. 227-246. Http://www.imagescience.org/meijering/publications/download/ijcv1999.pdf.
Kwon, Sung Min, et al., Digital Subtraction CT Angiography Based on Efficient 3D Registration and Refinement. Computerized Medical Imaging and Graphics 28 (2004) 391-400. Http://www-isl.kaist.ac.kr/Papers/IJ/ij57.pdf.
Boedeker, Kirsten, et al., SureSubtraction (TM) Digital Subtraction Angiography for CT. Toshiba White Paper 2007. Http://www.medical.toshiba.com/Downloads/Sure-Subtraction-White-Paper.pdf.
Tomandl, B.F., et al., Bone-Subtraction CT Angiography for the Evaluation of Intracranial Aneurysms. AJNR Am J Neroradiol 27:55-59, Jan. 2006. Http://www.ajnr.org/cgi/reprint/27/1/55.

* cited by examiner

*Primary Examiner* — Roberto Velez
(74) *Attorney, Agent, or Firm* — McAndrews, Held & Malloy, Ltd.; Rick Wascher

(57) ABSTRACT

Certain embodiments of the present invention provide systems, methods and computer instructions for detecting a pathological condition of a vasculature. Certain embodiments provide a method for detecting a pathological condition of a vasculature. The method includes accessing imaging data indicative of the vasculature and having a data type, selecting a detection process corresponding to the data type from among a plurality of detection processes, each of the detection processes processing data of a different data type. The method also includes processing the imaging data having the data type with the selected detection process, and superimposing the processed imaging data on the imaging data indicative of the pathological condition of the vasculature.

22 Claims, 3 Drawing Sheets

|  | NCT and CTA image data | Volume or Helical Shuttle CT Perfusion data | Dual Energy CTA image data | Dual Energy monochromatic image data |
| --- | --- | --- | --- | --- |
| Accessing image data | Thin-slice 3D data (e.g. 0.6-1.25 mm) | Retro-thin reformat to achieve higher spatial resolution (slice thickness of e.g. 0.6-1.25 mm) | Thin-slice 3D data (e.g. 0.6-1.25 mm) | Thin-slice 3D data (e.g. 0.6-1.25 mm) |
| Pre-processing image data | DSA with rigid registration | DSA with rigid registration, followed by the extraction of NCT, CTA, and CTV data sets | Separation of iodinated contrast from calcifications and bony structures | Extraction of monochromatic energy image data and displaying the basis material components in a fused color representation |
| Detecting aneurysms and/or lesions | Shape or texture-based detection algorithm | Shape or texture-based detection algorithm | Shape or texture-based detection algorithm | Shape or texture-based detection algorithm |
| Visualizing the anatomy | Displaying the extracted shapes or textures superimposed on the original vasculature | Displaying time-dependent washin and washout of contrast (arterial and venous phases) with the extracted shapes superimposed on the original vasculature | Displaying the extracted shapes or textures superimposed on the original vasculature | Displaying the extracted shapes or textures superimposed on the original vasculature |

SYSTEMS AND METHODS FOR AUTOMATED DIAGNOSIS

BACKGROUND OF THE INVENTION

Aneurysms are a fundamental cause of hemorrhagic stroke and accounts for about 20 percent of all stroke cases. If an aneurysm in the brain ruptures, a portion of the brain is filled with blood that can cause tissue death or pressure in the head. Large hemorrhages, generally caused by clearly visible large aneurysm, can also be fatal. A particular case of interest is the debilitating "dementia" like conditions caused by micro hemorrhages that are due to small aneurysm ruptures.

Aneurysms are infrequently encountered on a straight, non-branching segment of an intracranial artery. Aneurysms occurring on straight, non-branching segments are more often found to have sacs that point longitudinally along the walls of the artery in the direction of blood flow, and to project only minimally above the adventitial surface. Aneurysms having these characteristics are of a dissecting type, rather than of a congenital saccular type. The development of dissecting type aneurysms is heralded more frequently by the onset of ischemic neurological deficits than by the subarachnoid hemorrhage associated with congenital saccular aneurysms.

While the underlying mechanisms of aneurysm formation are generally unclear, aneurysms may often develop in association with arterio-venous malformations ("AVM"). AVM's generally consist of snarled tangles of cerebral arteries and veins, and/or spinal arteries and veins. Tangles of arteries and veins lack interconnecting capillary networks necessary to effectively control oxygen delivery to brain tissues.

In addition to oxygen tissue deprivation, rapid arterio-venous flow rates inside the AVM may cause dangerously high blood pressure and vessel wall weakness, potentially leading to vessel deterioration, venous stenosis, aneurysm formation, subsequent hemorrhage, and even stroke. AVM's account for approximately two percent of all hemorrhagic strokes that occur each year, and about one percent of those with AVM's will die as a direct result of AVM's.

Currently, acute stroke diagnosis using computed tomography ("CT") consists of utilizing non-contrast CT ("CT") imaging data to rule out cerebral hemorrhage, CT angiography ("CTA") imaging data to rule out brain aneurysm, dynamic CT perfusion imaging data to assess cerebral perfusion disturbances, and CTA and CT venography ("CTV") imaging data to rule out AVM's. For large brain coverage, a dynamic CT perfusion scan is generally administered with a volume shuttle protocol or mode. Other acquisition protocols for use in the CT perfusion scan include helical shuttle and dual energy CTA. These dynamic CT perfusion scan protocols have the ability to extract NCT, CTA, and CTV phases from data obtained from a dynamic CT perfusion scan, and thus potentially eliminate additional CTA and CTV scans.

Dual energy CTA provides an ability to separate iodine in a contrast-enhanced vasculature from calcium or bone, thereby removing ambiguities when signal levels between iodine and calcium are comparable. Dual energy CTA also provides an ability to reduce or eliminate beam-hardening effects, which are seen within the cranium.

BRIEF SUMMARY OF THE INVENTION

Certain embodiments of the present technology provide systems, methods and computer instructions for detecting a pathological condition of a vasculature.

In one embodiment, the invention provides a method for detecting a pathological condition of a vasculature. The method includes accessing imaging data indicative of the vasculature and having a data type, selecting a detection process corresponding to the data type from among a plurality of detection processes, each of the detection processes processing data of a different data type. The method also includes processing the imaging data having the data type with the selected detection process, and superimposing the processed imaging data on the imaging data indicative of the pathological condition of the vasculature. In some embodiments, the pathological condition of the vacation includes one of an aneurysm, arteriovascular malformation, and vasospasm.

In another embodiment, the invention provides a diagnostic system that includes a scanner and a processor. The scanner provides imaging data indicative of a pathological condition of a vasculature, and generates a data type corresponding to the imaging data. The processor processes the imaging data according to the datatype from among a plurality of processes, and each process detects a pathological characteristic. The processor superimposes the processed imaging data on the imaging data indicative of the pathological condition of the vasculature. In some embodiments, the pathological condition of the vacation includes one of an aneurysm, arteriovascular malformation, and vasospasm.

In yet another embodiment, the invention provides a computer-readable storage medium that includes instructions for execution on a processing device. The instructions include a scanning routine to provide imaging data indicative of a vasculature, and generate a data type corresponding to the imaging data. The instructions also include a processing routine to process the imaging data according to the data type from among a plurality of subroutines, each subroutine configured to detect a pathological characteristic, and to superimpose the processed imaging data on the imaging data indicative of a pathological condition of the vasculature. In some embodiments, the pathological condition of the vacation includes one of an aneurysm, arteriovascular malformation, and vasospasm.

BRIEF DESCRIPTION OF SEVERAL VIEWS OF THE DRAWINGS

FIG. 5 is a fable listing exemplary processing algorithms.

Figures 1, 2:
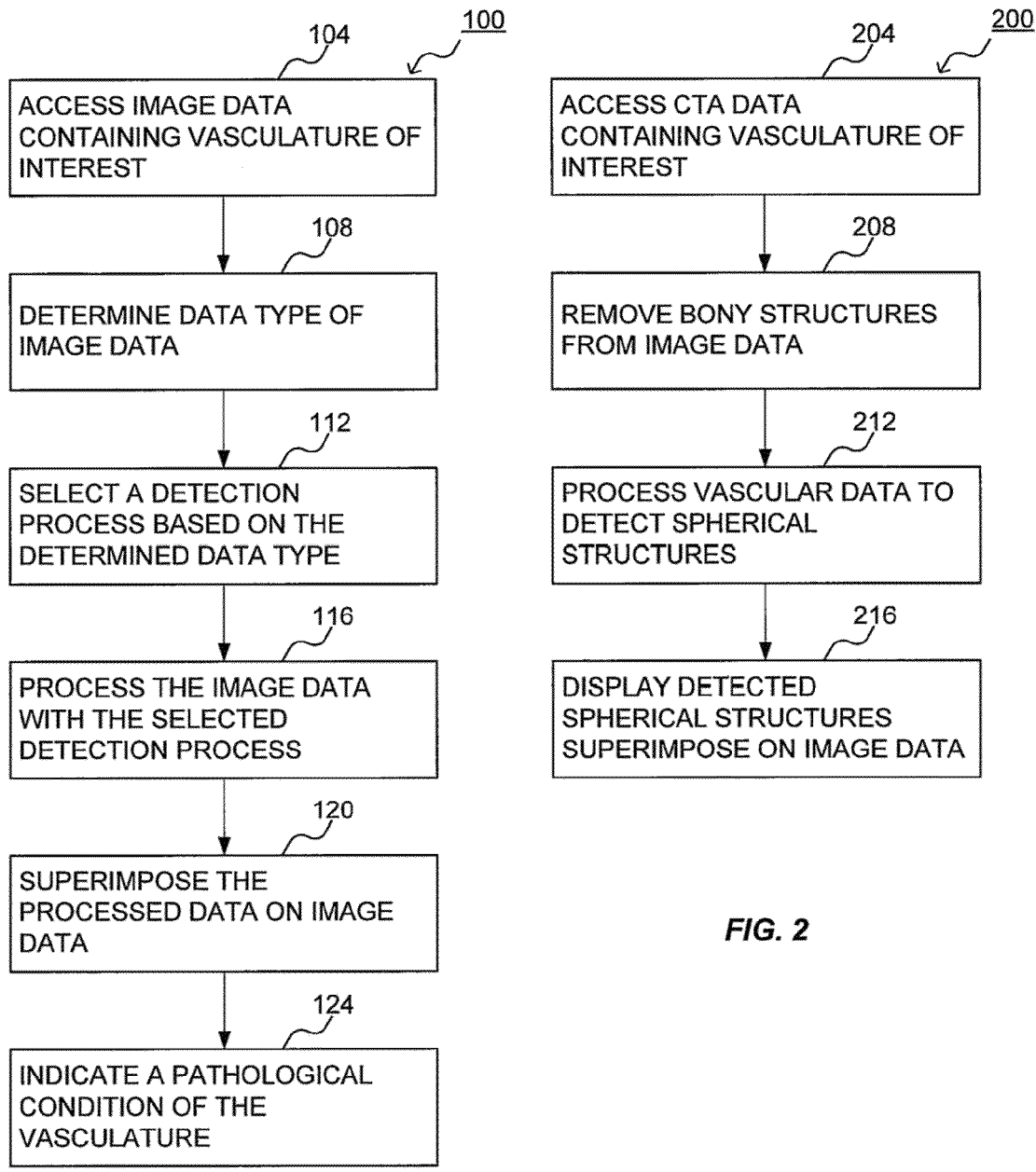
FIG. 1 is a flow diagram for a process for detecting a pathological condition of a vasculature used in accordance with embodiments of the present technology.
FIG. 2 is a flow diagram for a method of detecting a pathological condition of a vasculature using dual energy computed tomography angiography ("CTA") image data based on the method in FIG. 1.

The foregoing summary, as well as the following detailed description of certain embodiments of the present invention, will be better understood when read in conjunction with the appended drawings. For the purpose of illustrating the invention, certain embodiments are shown in the drawings. It should be understood, however, that the present invention is not limited to the arrangements and instrumentality shown in the attached drawings.

DETAILED DESCRIPTION OF THE INVENTION

While computed tomography ("CT") imaging data is typically stored centrally or distributed in hospital information systems ("HIS") or picture archiving and communication systems ("PACS"), diagnosis using CT imaging data often depends a type of the CT imaging data, an availability of the CT imaging data, different diagnosis algorithms, and hence different processing systems. Accordingly, automated and integrated software, methods, and systems for diagnosing brain aneurysms, brain lesions, AVM's, and vessel blockages using stored imaging data can dramatically improve and streamline clinical workflow and productivity in stroke assessment processes.

Certain embodiments of the present technology can provide an ability to access a plurality of imaging data of an anatomy, to preprocess these data using appropriate algorithms unique to each datatype, to detect pathological conditions such as, aneurysms, lesions, AVM's, vessel blockages, using shape and/or texture-based detection algorithm, and to visualize the anatomy using visualization techniques appropriate for each of data types. Exemplary data types include, but are not limited to, non-contrast CT ("NCT") and CT angiography ("CTA") image data, volume or helical shuttle image data, dual energy CTA image data, dual energy monochromatic image data, and the like.

An exemplary algorithm for processing NCT and CTA image data includes accessing three-dimensional ("3D") NCT and 3D CIA data sets indicative of an anatomy and containing, for example, a vasculature of interest, and pre-processing the 3D NOT and CTA data sets. In some embodiments, pre-processing includes registering 3D NCT and corresponding 3D CTA data sets, and removing bony structures from 3D CTA image data using both 3D NCT and 3D CTA data sets. The exemplary processing algorithm then detects one or more pathological conditions, such as, for example, aneurysms, and lesions. Detection of pathological conditions generally include processing the bone-removed 3D CTA data, and extracting spherical shapes or textures from the processed image data. In some cases, the exemplary processing algorithm visualizes the anatomy by displaying the extracted shapes superimposed on the original vasculature. Details of these processing algorithms are discussed below.

An exemplary algorithm for processing volume or helical shuttle image data includes accessing CT perfusion data indicative of an anatomy and containing, for example, a vasculature of interest, and pre-processing the CT perfusion data. For example, pre-processing includes registering the CT perfusion data, and extracting 3D NCT and 3D CTA image data sets from the CT perfusion data set, while keeping the CT perfusion data for four-dimensional ("4D") visualization and review. Pre-processing also includes removing any bony structures from the 3D CTA image data using both the 3D NCT and CTA data sets. The exemplary algorithm also detects pathological conditions, such as, for example, aneurysms, and lesions via processing the bone-removed 3D CTA data, and extracting spherical shapes and/or textures from the processed data. Thereafter, the exemplary algorithm also visualizes the anatomy, for example, by displaying time-dependent washins and washouts of contrast (arterial and venous phases) with the extracted shapes superimposed on the vasculature. Details of these processing algorithms are discussed below.

An exemplary algorithm for processing dual energy CTA image data includes accessing dual energy 3D CTA image data indicative of an anatomy and containing, for example, a vasculature of interest, and pre-processing the dual energy 3D CTA image data. In some cases, pre-processing includes separating iodinated contrast-enhanced data, such as, for example, CTA data, from calcifications and bony structures, and processing the 3D CTA data and extracting spherical shapes and/or textures. Thereafter, the exemplary algorithm also visualizes the anatomy, for example, by displaying the extracted shapes superimposed on the vasculature. Details of these processing algorithms are discussed below.

An exemplary algorithm for processing dual energy monochromatic image data includes accessing dual energy 3D CTA image data indicative of an anatomy and containing, for example, a vasculature of interest, and pre-processing the dual energy 3D CTA image data. In some cases, pre-processing includes extracting a monochromatic energy image corresponding to contrast-enhanced data (CIA without bone) with minimum artifacts due to beam hardening effects, and displaying a plurality of basis material components in a fused color representation. The algorithm also processes the dual energy monochromatic 3D CTA data to extract spherical shapes and/or textures, and visualizes the anatomy, for example, by displaying the extracted shapes superimposed on the original vasculature.

FIG. 1 is a flow diagram for a process 100 for detecting a pathological condition of a vasculature used in accordance with embodiments of the present technology. The detection process 100 begins with accessing imaging data containing the vasculature of interest, at block 104. Although the imaging data generally is obtained from a computed tomography ("CT") scanner, the imaging data can also be obtained with other scanning techniques. Depending on techniques used during scanning, different imaging data types can be obtained. Exemplary data types include, but are not limited to, non-contrast CT ("NCT") type, CT angiography ("CTA") type, volume axial shuttle type, volume helical shuttle type, dynamic CTA data, dual energy CTA type, dual energy monochromatic type, and the like.

The detection process 100 then determines a data type of the accessed imaging data at block 108, selects a type-dependent detection algorithm or process based on the data type at block 112, and processes the imaging data with the selected type-dependent detection algorithm at block 116. In some embodiments, the type-dependent detection algorithm uses a rigid registration algorithm for NCT and CTA, volume axial shuttle image data, and volume helical shuttle image data.

The rigid model-based spatial (3D/3D) registration is performed to register two static tomographic data sets such as NCI and CTA. For dynamically acquired data sets such as volume or helical shuttle CT perfusion data, spatial (3D/3D) registration is extended to include the time dimension. Exemplary rigid registration methods include, but are not limited to, landmark-based registration, segmentation-based registration, voxel property-based registration.

Landmark-based registration is based on a limited set of identified points, or landmarks, in the image data set. The landmarks can be anatomical, i.e. salient and accurately locatable points of the morphology of the visible anatomy. The landmarks can also be geometrical, i.e. points at the locus of the optimum of some geometric property. The set of identified landmarks is sparse compared to the original image content, which makes for relatively fast optimization procedures. Such algorithms optimize measures such as the average distance (L2 norm) between a landmark and the closest counterpart of the landmark, a Procrustean metric, or iterated minimal landmark distances. For the optimization of the latter measure, the iterative closest point ("ICP") algorithm and derived methods are popular. A Procrustean optimum can be computed or determined using Arun's method, but is more commonly searched for using general optimization techniques. Other methods perform landmark registration by testing a number of likely transformation hypotheses, which can e.g. be formulated by aligning three randomly picked points from each point set involved. Common optimization methods include quasi-exhaustive searches, graph matching and dynamic programming methods.

Segmentation-based registration is an extension of landmark-based registration, and is based on the extraction of higher-order structures such as curves, surfaces, or volumes as landmarks. In the rigid model-based approach, anatomically identical structures are extracted from both image sets to be registered, and used as a sole input for an alignment procedure. Although other registration models, such as, for example, deformable model and Chamfer matching technique, exist, rigid model approaches tend to be popular methods in the clinical use in neuro-imaging.

Voxel property-based registration methods operate directly on gray values of the image data, without prior data reduction by user or segmentation. These methods are generally subdivided into two distinct approaches. The first approach reduces immediately the image gray value content to a representative set of scalars and orientations. The second approach uses all of the image data, or the full image content, throughout the registration process.

Principal axes and moment-based methods are examples of reductive registration methods. These methods determine a center of gravity and a plurality of principal axis from moments, such as, for example, zeroth and first order moments, of the image data. Registration is then performed by aligning the center of gravity and the principal axes. In some cases, higher order moments are also computed and used in the registration process. Moment-based methods can also use segmented or binarized image data as input. Voxel property based methods using the full image content generally require minimum or no data reduction, but use all of the available information throughout the registration process. Exemplary paradigms that can be used for full image content registration include cross-correlation, Fourier domain based cross-correlation, and phase-only correlation, minimization of variance of intensity ratios, minimization of variance of grey values within segments, minimization of the histogram entropy of difference images, histogram clustering and minimization of histogram dispersion, maximization of mutual information, maximization of zero crossings in difference images, cepstral echo filtering, determination of the optic flow field, and the like.

Whether landmark, segmentation, or voxel property based registration method is used, parameters that make up the registration are typically determined through an optimization procedure. Exemplary optimization procedures include, but are not limited to, Powell's methods, the Downhill Simplex method. Brent's method and series of one-dimensional searches, Levenberg-Marquardt optimization, Newton-Raphson iteration, stochastic search methods, gradient descent methods, genetic methods, simulated annealing, geometric hashing, and quasi-exhaustive search methods. Frequent additions are multi-resolution and multi-scale approaches to speed up convergence, to reduce the number of transformations to be examined and to avoid local minima. For the rigid registration model, the ICP algorithm can be useful.

After the registration of the image data, the type-dependent detection algorithm as used in block 116 also includes extraction of NCT and CTA data from CT perfusion data including volume axial shuttle image data and volume helical shuttle image data. In some embodiments, the registered shuttle data can be used to extract a baseline non-contrast volume and a contrast-enhanced volume using a time density curve of a detected vessel. 3D NCT image data, corresponding to the head volume acquired during the first (contrast-free) phase of a dynamic acquisition, is extracted from the CT perfusion data set. Subsequently, CTA data is also extracted from the CT perfusion image data by locating the dynamic acquisition phase associated with a peak arterial concentration of contrast. Similarly, the CT venography ("CTV") data is also extracted from the dynamic acquisition data using the peak venous phase.

In some embodiments, the process in block 116 also includes a plurality of bone removal algorithms, such as, for example, digital subtraction angiography ("DSA,") for 3D NCT and CTA image data, volume axial shuttle data, and volume helical shuttle data having NCT and CTA data extracted, and dual energy bone removal algorithm for dual energy CTA image data.

Digital subtraction angiography ("DSA") algorithm for removing bone involves two co-registered data sets, NCT and contrast-enhanced CT ("CTA") image data. Bone masking in CTA image data is based on a continuous look-up table ("LUT"). In some embodiments, the LUT contains a set of factors B associated with various Hounsfield units CHIP) in the NCT data. In some cases, B is a linear function of HU, is equal to 0 when the NCT data has a value that is less than 40 HU, and has value of about 1 when the NCT has a value that is greater than 120 HU. A bone is removed by multiplying the CTA data by (1−B), where B is chosen based on the corresponding NCT HU in the LUT. The bone masking technique allows less sensitivity to spatial resolution, registration, and thresholding parameters. The bone masking technique also generally produces smoother images with fewer artifacts. Resulting bone-free 3D image data generally contains contrast-enhanced vasculature and brain tissue. In the case of dynamic volume axial shuttle data, or volume helical shuttle data, the abovementioned DSA algorithm is applied to the extracted NCI data and the corresponding CTA volume at every other temporal step.

CTA data acquired with two peak-kilovoltage ("kVp") levels is applied to a basis material decomposition algorithm to generate material density images such as water and iodine, as well as monochromatic representations. Conventional hierarchical bone removal algorithms are threshold-based, and rely on a priori knowledge of the head and neck anatomy. As such, hone removal is not always robust, particularly when the CT number of the iodine in blood is similar to the surrounding bone, resulting in segmentation errors. By combining dual energy basis material decomposition with the bone removal algorithms, a more accurate segmentation is possible. This is accomplished by taking the iodine and water basis material images and creating a mask that can be used to correctly label iodine-containing structures (i.e. vessels).

Thereafter, the type-dependent algorithms also detect one or more pathological conditions such as, for example, aneurysms, lesions, and AVM's. To detect the pathological conditions, shapes and textures are extracted from the bone-removed CTA data, or from the volume axial shuttle image or volume helical shuttle image, in some embodiments, methods as described in U.S. Publication No. 2006/0079743 by Ferrant et al, which published on Apr. 13, 2006, the entire contents of which are incorporated herein by reference, are used to extract different shapes and textures.

The extraction methods, as described in U.S. Publication No. 2006/0079743, use a priori anatomical information to reduce overlapping of disparate responses. Specifically, 3D responses are determined using formulation with local curvature at implicit isosurfaces. A curvature tensor determines a plurality of local curvatures, such as, $k_{min}$ and $k_{max}$ in the null space of the gradient. The respective curvatures can be determined using EQN. (1) as follows.

$$k_i = (\min \hat{v}, \max \hat{v}) \frac{-\hat{v}^T N^T H N \hat{v}}{\|\nabla I\|} \quad (1)$$

Where k is the curvature, v is a vector in the N null space of the gradient of image data I with H being its Hessian. The solutions to EQN. (1) are the Eigen values of EQN. (2) as follows.

$$\frac{-N^T H N}{\|\nabla I\|} \quad (2)$$

The responses of the curvature tensor and $k_{min}$ and $k_{max}$) are segregated into spherical and cylindrical responses based on thresholds on $k_{min}$ and $k_{max}$, and the ratio of $k_{min}$ to $k_{max}$ derived from the size and aspect ratio of the sphericalness and cylindricalness of interest. In one exemplary embodiment, the ratio of $k_{min}/k_{max}$ is 2:1, and a minimum spherical diameter of 1 mm with a maximum of 20 mm is used. It should be noted that other combinations result in different shape response characteristics depending on different anatomical objects.

The established disparate responses have overlapping regions that can be termed as false responses. Different acquisition parameters, recon algorithm, and their noise characteristics are major sources of these false responses. A method of removing the false responses is to tweak the threshold values to compensate for the differing acquisitions. Tweaking threshold values generally involves creating a mapping of the thresholds to all possible acquisition. However, such mapping is generally an intractable problem. Other solutions utilizes anatomical information in the form of a scale of the responses on large vessels, such as, for example, cylindrical responses, and the intentional biasing of the response towards spherical vs. cylindrical to come up with the use of morphological closing of the cylindrical response volume to cull any spherical responses that are in the intersection of the "closed" cylindrical responses and the spherical response.

Other types of pathological condition detection algorithm includes a detection process for arterio-venous malformations ("AVM") for use with bone-removed CTA and CTV image data obtained from DSA, and CTV data extracted from volume or helical shuttle data. In some embodiments, AVM's are detected by determining an intersection of the CTA and CTV vasculature at all phase levels, for example, peak arterial to peak venous phases. The determined intersections generally represent entangled bundles of vessels with blood recirculation that does not pass through associated brain tissues. In other embodiments, texture detection algorithms are used to determine lesions corresponding to hemorrhage or infarct. A texture algorithm utilizes contextual information in the pattern of densities that can be extracted using ordered statistics. Matching the ordered statistics to known values provides the detection capability.

Referring back to FIG. 1, after the process 100 has processed the image data to obtain data of interest indicative of the pathological condition, the process 100 proceeds to superimpose the processed data on the image data at block 120, and indicates the detected pathological condition, such as, for example, aneurysm, arteriovascular malformation, and vasospasm, at block 124.

For example, for NCT and CTA image data, and dual energy CTA image data, the extracted shapes corresponding to aneurysms, AVM's, other vessel occlusions, infarct or hemorrhagic lesions, are superimposed on the vasculature (or brain tissue) of interest for visualization. Vessels with aneurysm, or AVM are segmented and displayed in various views including VR, 3D MIP, and axial, coronal, sagittal and oblique view's. For another example, for volume or helical shuttle image data, bone-removed CT perfusion data is dynamically displayed to show washin and washout of contrast in the brain vasculature, enabling the visualization of both arterial and venous phases. The extracted shapes corresponding to aneurysms, AVM's, other vessel occlusions, infarct or hemorrhagic lesions, are superimposed on the vasculature of interest (or brain tissue). The vessel with aneurysm, or AVM are segmented and displayed in various views including VR, 3D MIP, and axial, coronal, sagittal, and oblique views.

Figure 3:
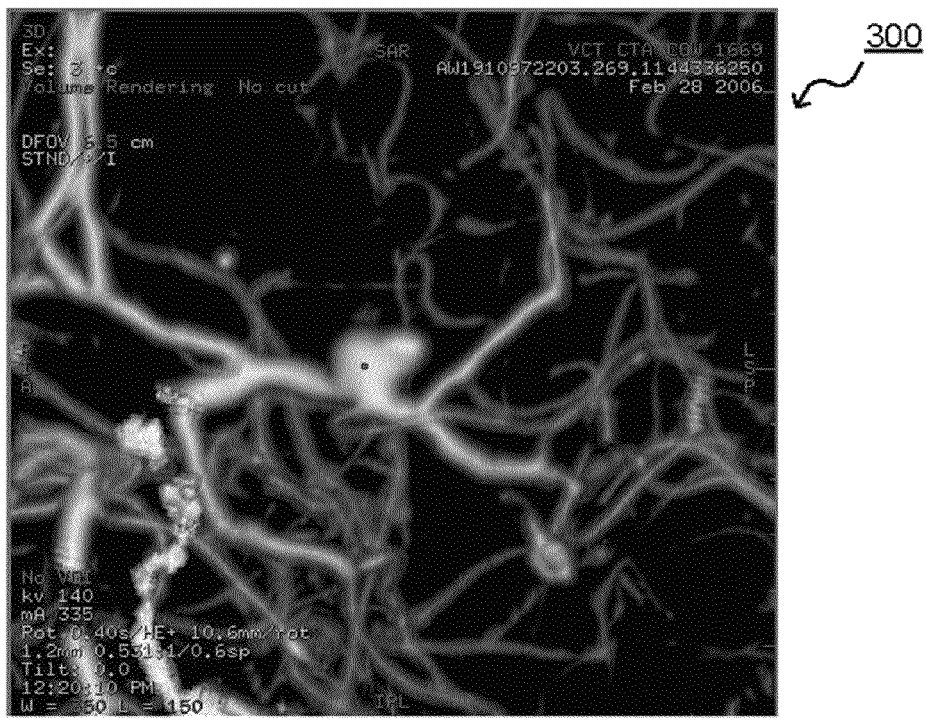
FIG. 3 is a visualization of a vasculature used in accordance with embodiments of the present technology.
Figure 4:
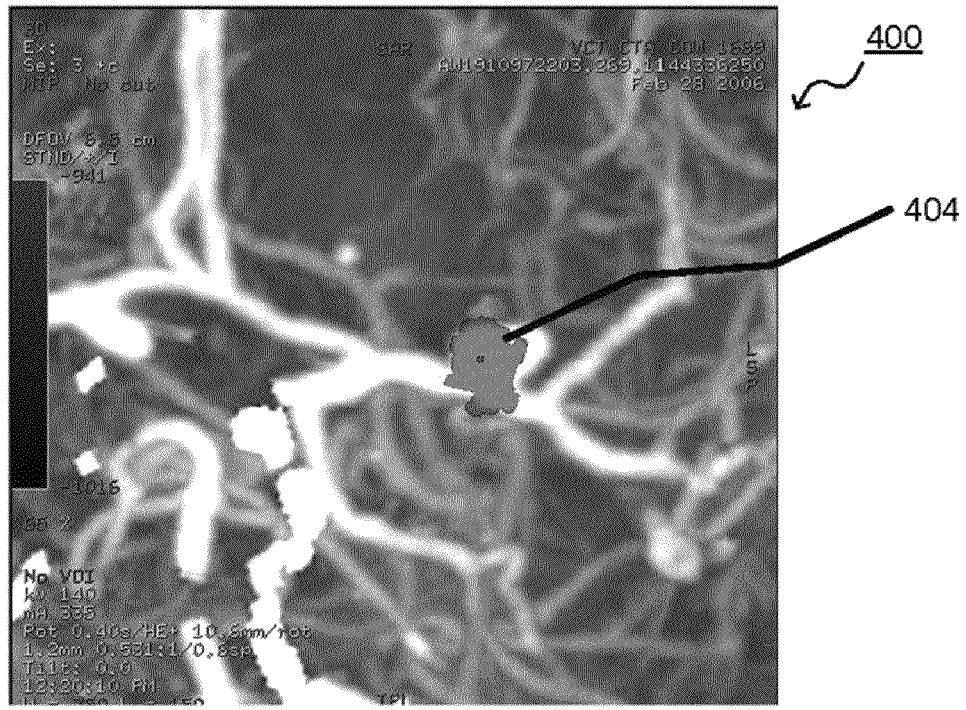
FIG. 4 is a visualization of a pathological condition superimposed on the vasculature of FIG. 3 used in accordance with embodiments of the present technology.

FIG. 2 is a flow diagram for a method or process 200 of detecting a pathological condition of a vasculature using dual energy computed tomography angiography ("CTA") image data based on the method in FIG. 1. At block 204, the detection process 200 accesses CTA data that contains a vasculature of interest after a CTA data type has been determined. Bony structures from the CTA data are removed at block 208, and spherical shapes of vasculature are extracted, as discussed earlier, at block 212. Thereafter, the process 200 displays a superimposed structure on the image data at block 216. FIG. 3 is a visualization of a vasculature before detection 400, and FIG. 4 is visualization 400 of a pathological condition 404 superimposed on the vasculature of FIG. 3.

Thus, certain embodiments provide a technical effect of detection a pathological condition of a vasculature using a computer. Certain embodiments provide a technical effect of enabling an automated and integrated system for detecting a pathological condition of a vasculature given image data of the vasculature. The system automatically selects an appropriate and specific type of diagnosis process, and displays one or more resulting images indicative of the diagnosis.

FIG. 5 is a table listing exemplary processing algorithms and corresponding processing parameters for use with embodiments of the present technology, such as the method in FIG. 1, for example.

Certain embodiments contemplate methods, systems and computer program products on any machine-readable media to implement functionality described above. Certain embodiments may be implemented using an existing computer processor, or by a special purpose computer processor incorporated for this or another purpose or by a hardwired and/or firmware system, for example.

Certain embodiments include computer-readable media for carrying or having computer-executable instructions or data structures stored thereon. Such computer-readable media may be any available media that may be accessed by a general purpose or special purpose computer or other machine with a processor. By way of example, such computer-readable media may comprise RAM, ROM, FROM, EPROM, EEPROM, Flash, CD-ROM or other optical disk storage, magnetic disk storage or other magnetic storage devices, or any other medium which can be used to carry or store desired program code in the form of computer-executable instructions or data structures and which can be accessed by a general purpose or special purpose computer or other machine with a processor. Combinations of the above are also included within the scope of computer-readable media. Computer-executable instructions comprise, for example, instructions and data which cause a general purpose computer, special purpose computer, or special purpose processing machines to perform a certain function or group of functions.

Generally, computer-executable instructions include routines, programs, objects, components, data, structures, etc., that perform particular tasks or implement particular abstract data types. Computer-executable instructions, associated data structures, and program modules represent examples of program code for executing steps of certain methods and systems disclosed herein. The particular sequence of such executable instructions or associated data structures represent examples of corresponding acts for implementing the functions described in such steps.

Embodiments of the present invention may be practiced in a networked environment using logical connections to one or more remote computers having processors. Logical connections may include a local area network (LAN) and a wide area network (WAN) that are presented here by way of example and not limitation. Such networking environments are commonplace in office-wide or enterprise-wide computer networks, intranets and the Internet and may use a wide variety of different communication protocols. Those skilled in the art will appreciate that such network computing environments will typically encompass many types of computer system configurations, including personal computers, hand-held devices, multi-processor systems, microprocessor-based or programmable consumer electronics, network PCs, minicomputers, mainframe computers, and the like. Embodiments of the invention may also be practiced in distributed computing environments where tasks are performed by local and remote processing devices that are linked (either by hardwired links, wireless links, or by a combination of hardwired or wireless links) through a communications network. In a distributed computing environment, program modules may be located in both local and remote memory storage devices.

An exemplary system for implementing the overall system or portions of the invention might include a general purpose computing device in the form of a computer, including a processing unit, a system memory, and a system bus that couples various system components including the system memory to the processing unit. The system memory may include read only memory (ROM) and random access memory (RAM). The computer may also include a magnetic hard disk drive for reading from and writing to a magnetic hard disk, a magnetic disk drive for reading from or writing to a removable magnetic disk, and an optical disk drive for reading from or writing to a removable optical disk such as a CD ROM or other optical media. The drives and their associated computer-readable media provide nonvolatile storage of computer-executable instructions, data structures, program modules and other data for the computer.

While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

The invention claimed is:

1. A method for detecting a pathological condition of a vasculature using a computer, the method comprising:
performing by at least one computer processor, at least:
accessing imaging data indicative of the vasculature and having one of a plurality of data types, each of the plurality of data types corresponding to a different scanning technique used to acquire the imaging data;
automatically selecting a detection process corresponding to the data type of the imaging data from among a plurality of detection processes, each of the detection processes processing data of a different data type;
processing the imaging data having the data type with the selected detection process; and
superimposing the processed imaging data on the imaging data indicative of the pathological condition of the vasculature.

2. The method of claim 1, wherein the pathological condition of the vasculature comprises one of an aneurysm, arteriovascular malformation, and vasospasm.

3. The method of claim 1, further comprising scanning the vasculature with a computed tomography ("CT") scanner, and wherein the data type comprises at least one of non-contrast CT ("NCT") data, CT angiography ("CTA") data, volume axial shuttle data, volume helical shuttle data, dynamic CTA data, dual energy CTA data, and dual energy monochromatic data.

4. The method of claim 3, wherein the data type comprises at least one of NCT data with corresponding CTA, volume shuttle data, and helical shuttle data, and wherein processing the imaging data comprises registering the imaging data based on at least one of a landmark, segmentation, and voxel property.

5. The method of claim 3, wherein the data type comprises at least one of NCT data with corresponding CTA, volume shuttle data, and helical shuttle data, and wherein processing the imaging data comprises removing data indicative of a bony structure from the imaging data.

6. The method of claim 5, wherein processing the imaging data further comprises extracting at least one of a spherical shape and texture.

7. The method of claim 3, wherein the data type comprises at least one of volume shuttle data and helical shuttle data, and wherein processing the imaging data comprises extracting NCT and CTA data from the imaging data.

8. The method of claim 7, wherein processing the imaging data further comprises:
extracting a CT venography ("CTV") from the imaging data; and
determining intersection of the CTV and CTA.

9. A diagnostic system comprising:
a scanner configured to provide imaging data indicative of a pathological condition of a vasculature, and generate one of a plurality of data types corresponding to the imaging data, each of the plurality of data types corresponding to a different scanning technique used to acquire the imaging data; and
a processor configured to:
automatically select a process corresponding to the data type of the imaging data from among a plurality of processes, each of the processes processing data of a different data type, each process configured to detect a pathological characteristic,
process the imaging data according to the selected process, and
superimpose the processed imaging data on the imaging data indicative of the pathological condition of the vasculature.

10. The system of claim 9, wherein the scanner comprises a computed tomography ("CT") scanner, and wherein the data type comprises at least one of non-contrast CT ("NCT") data, CT angiography ("CTA") data, volume axial shuttle data, volume helical shuttle data, dynamic CTA data, dual energy CTA data, and dual energy monochromatic data.

11. The system of claim 10, wherein the data type comprises at least one of NCT data with corresponding CTA, volume shuttle data, and helical shuttle data, and wherein the processor is further configured to register the imaging data based on at least one of a landmark, segmentation, and voxel property.

12. The system of claim 11, wherein the processor is further configured to extract at least one of a spherical shape and texture.

13. The system of claim 10, wherein the data type comprises at least one of NCT data with corresponding CTA, volume shuttle data, and helical shuttle data, and wherein the processor is further configured to remove data indicative of bony structures from the imaging data.

14. The system of claim 10, wherein the data type comprises at least one of a volume shuttle data and helical shuttle data, and wherein the processor is further configured to extract NCT and CTA data from the imaging data.

15. The system of claim 14, wherein the processor is further configured to extract a CT venography ("CTV") from the imaging data, and to determine intersection of the CTV and CTA.

16. The system of claim 9, wherein the pathological condition of the vasculature comprises one of an aneurysm, arteriovascular malformation, and vasospasm.

17. A non-transitory computer-readable storage medium including instructions for execution on a processing device, the instructions comprising:
   a scanning routine configured to provide imaging data indicative of a vasculature, and generate one of a plurality of data types corresponding to the imaging data, each of the plurality of data types corresponding to a different scanning technique used to acquire the imaging data; and
   a processing routine configured to:
      automatically select a subroutine corresponding to the data type of the imaging data from among a plurality of subroutines, each of the subroutines processing data of a different data type, each subroutine configured to detect a pathological characteristic,
      process the imaging data according to the selected subroutine, and
      superimpose the processed imaging data on the imaging data indicative of a pathological condition of the vasculature.

18. The non-transitory computer-readable storage medium of claim 17, wherein the scanning routine comprises a computed tomography ("CT") scanning routine, and wherein the data type comprises at least one of non-contrast CT ("NCT") data, CT angiography ("CTA") data, volume axial shuttle data, volume helical shuttle data, dynamic CTA data, dual energy CTA data, and dual energy monochromatic data.

19. The non-transitory computer-readable storage medium of claim 18, wherein the data type comprises at least one of NCT data with corresponding CTA, volume shuttle data, and helical shuttle data, and wherein the processor is further configured to remove data indicative of bony structures from the imaging data.

20. The non-transitory computer-readable storage medium of claim 19, wherein the processing routine is further configured to extract at least one of a spherical shape and texture.

21. The non-transitory computer-readable storage medium of claim 17, wherein the data type comprises at least one of a volume shuttle data and helical shuttle data, wherein the processing routine is further configured to extract NCT and CTA data from the imaging data; and wherein the processing routine is further configured to extract a CT venography ("CTV") from the imaging data, and to determine intersection of the CTV and CTA.

22. The non-transitory computer-readable storage medium of claim 17, wherein the pathological condition of the vasculature comprises one of an aneurysm, arteriovascular malformation, and vasospasm.

* * * * *